(12) United States Patent
Kwon

(10) Patent No.: US 8,445,643 B2
(45) Date of Patent: May 21, 2013

(54) ANTI-IRC85 MONOCLONAL ANTIBODY; AND COMPOSITION COMPRISING THE SAME FOR PREVENTING AND TREATING TUBERCULOSIS OR ENTERITIS DISEASE; AND THE USE THEREOF

(75) Inventor: Byoung Se Kwon, Gyeonggi-do (KR)

(73) Assignee: Bio-Support Co., Ltd., Gyeonggi-do (KR)

( * ) Notice: Subject to any disclaimer, the term of this patent is extended or adjusted under 35 U.S.C. 154(b) by 671 days.

(21) Appl. No.: 12/596,747

(22) PCT Filed: Apr. 24, 2008

(86) PCT No.: PCT/KR2008/002334
§ 371 (c)(1),
(2), (4) Date: Oct. 20, 2009

(87) PCT Pub. No.: WO2008/130204
PCT Pub. Date: Oct. 30, 2008

(65) Prior Publication Data
US 2010/0291101 A1 Nov. 18, 2010

(30) Foreign Application Priority Data

Apr. 24, 2007 (KR) .......... 10-2007-0039791
Apr. 24, 2008 (KR) .......... 10-2008-0037968

(51) Int. Cl.
*C07K 16/00* (2006.01)
*C12P 21/08* (2006.01)

(52) U.S. Cl.
USPC ............. 530/387.1; 530/387.9; 530/388.22

(58) Field of Classification Search
None
See application file for complete search history.

(56) References Cited

U.S. PATENT DOCUMENTS 5,859,205 A * 1/1999 Adair et al. ............. 530/387.3

FOREIGN PATENT DOCUMENTS

WO WO 2007019901 A1 * 2/2007

OTHER PUBLICATIONS

Brown et al. "Tolerance to Single, but not multiple, amino acid replacements in antibody VH CDR2" J. Immuno, 1996, 156: pp. 3285-3291.*
Eduardo Padlan, "Anatomy of the antibody molecule" Molecular Immun. 31(3) (1994), pp. 169-217.*
Vajdos et al. "Comprehensive functional maps of the antigen-binding site of an anti-ErbB2 antibody obtained with shotgun scanning mutagenesis" J. Mol. Biol. (2002) 320, pp. 415-428.*
Burman, W. "The value of in vitro drug activity and pharmacokinetics in predicting the effectiveness of antimycobacterial therapy: a critcal review" Am J Med Sci 313, 1997, 355-363.*
Reilly et al. "Oral devliery of antibodies" Clin, Pharmacokinet. 1997, 32(4): 313-323.*
Y.M. Song; "Identification of counterpart of IRC85Z39Ig/CRIg/VSIG4 and in vitro killing of intracellular *Listeria monocytogens* by IRC85 signaling on monocytes", Master of Science Thesis, University of Ulsan(Rep. of Korea), Department of Immunology and Biomedicine, Feb. 2007 (exact date not available).
Jin-Kyung Kim, et al; "Characterization of monoclonal antibody specific to the Z39Ig protein, a member of immunoglobulin superfamily", Immunology Letters, vol. 99(2), pp. 153-161, Jul. 15, 2005.
Lorenz Vogt, et al; "VSIG4, a B7 family-related protein, is a negative regulator of T cell activation", Journal of Clinical Investigation, vol. 116(10), pp. 2817-2826, Oct. 2, 2006.
Min-Young Lee, et al; "Z39Ig is expressed on macrophages and may mediate inflammatory reactions in arthritis and atherosclerosis", Journal of Leukocyte Biology, vol. 80(4), pp. 922-928, Aug. 1, 2006.
Karim Y. Helmy, et al; "CRIg: A Macrophage Complement Receptor Required for Phagocytosis of Circulating Pathogens", Cell, vol. 124(5), pp. 915-927, Mar. 10, 2006.
International Search Report: mailed Sep. 29, 2008; PCT/KR2008/002334.

* cited by examiner

*Primary Examiner* — Maher Haddad
*Assistant Examiner* — James Rogers
(74) *Attorney, Agent, or Firm* — Ladas & Parry LLP

(57) ABSTRACT

The present invention provides the novel anti-IRC85 monoclonal antibody specifically binding with IRC85 and it showed potent effect in removing the infected/phagocytosed bacteria from THP-I, a monocytic cell that expresses human IRC85 and is infected with *Listeria monocytogenes* or WR-tubercle bacillus. Accordingly, it can be useful as a medicament and health care food in the prevention and treatment of tuberculosis disease and enteritis disease.

5 Claims, 5 Drawing Sheets

Figure 1

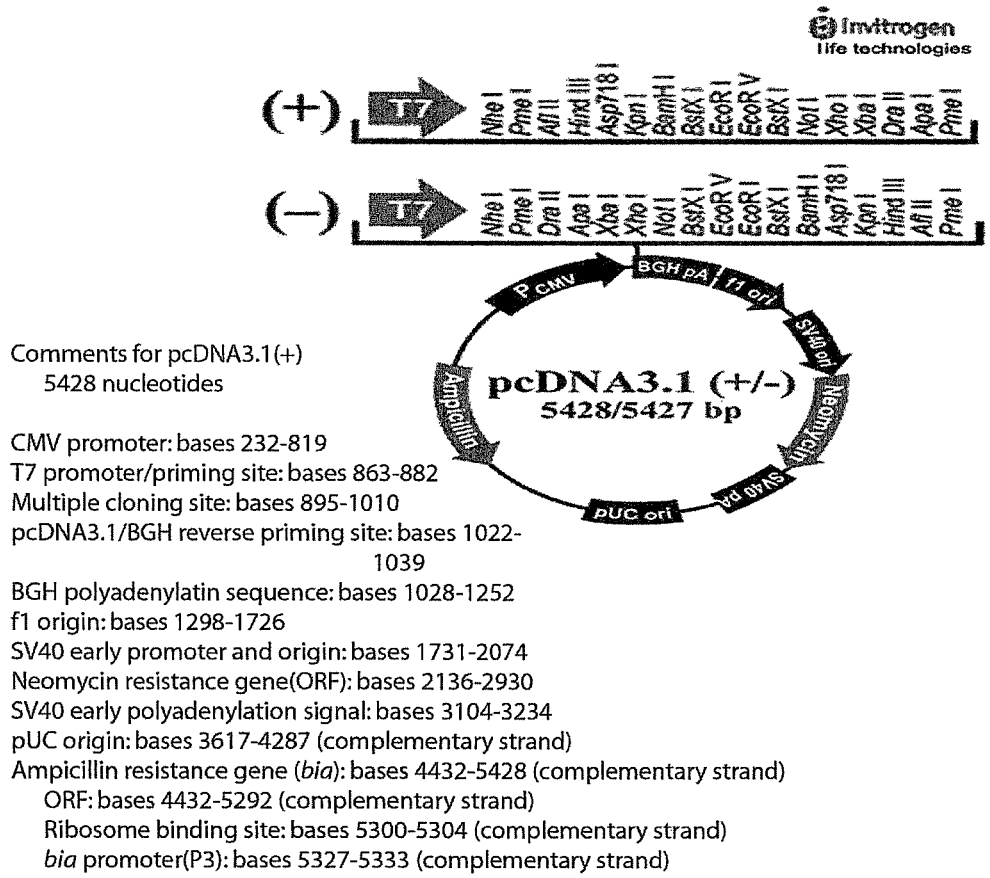

Comments for pcDNA3.1(+)
  5428 nucleotides

CMV promoter: bases 232-819
T7 promoter/priming site: bases 863-882
Multiple cloning site: bases 895-1010
pcDNA3.1/BGH reverse priming site: bases 1022-
  1039
BGH polyadenylatin sequence: bases 1028-1252
f1 origin: bases 1298-1726
SV40 early promoter and origin: bases 1731-2074
Neomycin resistance gene(ORF): bases 2136-2930
SV40 early polyadenylation signal: bases 3104-3234
pUC origin: bases 3617-4287 (complementary strand)
Ampicillin resistance gene (bia): bases 4432-5428 (complementary strand)
  ORF: bases 4432-5292 (complementary strand)
  Ribosome binding site: bases 5300-5304 (complementary strand)
  bia promoter(P3): bases 5327-5333 (complementary strand)

Figure 2

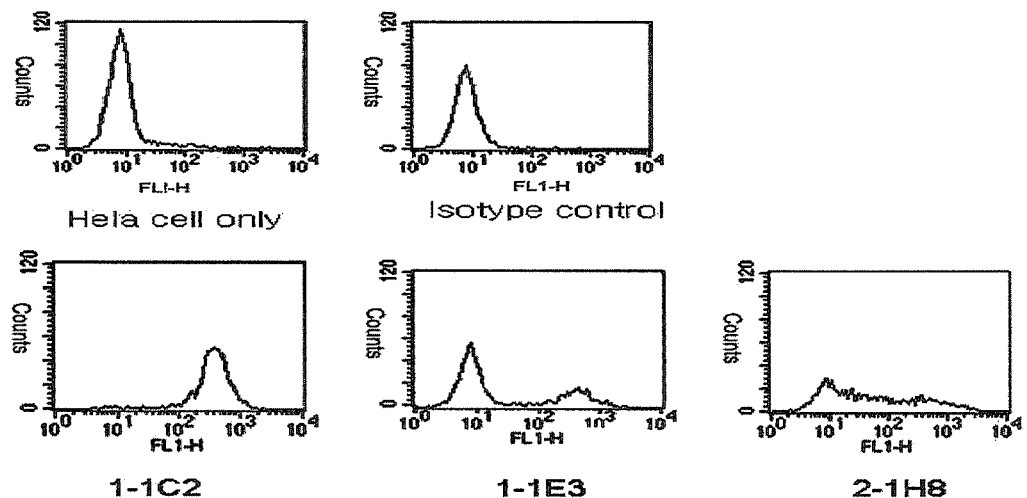

Extracellular domain of IRC85 was expressed in *E. coli*. His-tagged IRC85 extracellar domain was purified with Ni⁺-NTA column

SEQUENCE LISTING

```
<160> NUMBER OF SEQ ID NOS: 23

<210> SEQ ID NO 1
<211> LENGTH: 44
<212> TYPE: DNA
<213> ORGANISM: Artificial Sequence
<220> FEATURE:
<223> OTHER INFORMATION: sense primer for IRC85

<400> SEQUENCE: 1
cgggatccga attcggtacc cgtcccatcc tggaagtgcc agag                44

<210> SEQ ID NO 2
<211> LENGTH: 43
<212> TYPE: DNA
<213> ORGANISM: Artificial Sequence
<220> FEATURE:
<223> OTHER INFORMATION: anti-sense primer for IRC85

<400> SEQUENCE: 2
cgggatccga attcggtacg atgaagttgc cattctgcct gcc                 43

<210> SEQ ID NO 3
<211> LENGTH: 27
<212> TYPE: DNA
<213> ORGANISM: Artificial Sequence
<220> FEATURE:
<223> OTHER INFORMATION: His-sense primer for IRC85

<400> SEQUENCE: 3
cgcggatccc agcaggcaaa gtaccag                                   27

<210> SEQ ID NO 4
<211> LENGTH: 26
<212> TYPE: DNA
<213> ORGANISM: Artificial Sequence
<220> FEATURE:
<223> OTHER INFORMATION: His anti-sense primer for IRC85
```

<400> SEQUENCE: 4
gacaagcttc aggctctttc ctggcc         26

<210> SEQ ID NO 5
<211> LENGTH: 464
<212> TYPE: PRT
<213> ORGANISM: Artificial Sequence
<220> FEATURE:
<223> OTHER INFORMATION: 464 a.a. heavy chain for 6H8

<400> SEQUENCE: 5

```
Met Gly Arg Leu Thr Ser Ser Phe Leu Leu Ile Val Pro Ala Tyr
 1               5                  10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Ile Ser Leu
        35                  40                  45

Thr Thr Ser Gly Met Gly Val Gly Trp Ile Arg Gln Pro Ser Gly Glu
    50                  55                  60

Gly Leu Glu Trp Leu Ala Asp Ile Phe Trp Asp Asp Asn Lys Tyr Tyr
65                  70                  75                  80

Asn Pro Ser Leu Lys Ser Arg Leu Thr Ile Ser Lys Asp Thr Ser Thr
                85                  90                  95

Lys Gln Val Phe Phe Lys Ile Thr Ser Val Asp Thr Ala Asp Thr Ala
            100                 105                 110

Thr Tyr Tyr Cys Val Arg Val Tyr Tyr Lys Asn Asp Gly Tyr Phe Asp
        115                 120                 125

Val Trp Gly Ala Gly Thr Thr Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
    275                 280                 285

Glu Val Gln Phe Ser Trp Phe Val Asp Asp Val Glu Val His Thr Ala
290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350
```

-continued

```
Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
435                 440                 445

Leu His Asn His His Thr Glu Lys Ser Leu Ser His Ser Pro Gly Lys
450                 455                 460
```

<210> SEQ ID NO 6
<211> LENGTH: 238
<212> TYPE: PRT
<213> ORGANISM: Artificial Sequence
<220> FEATURE:
<223> OTHER INFORMATION: 238 a.a. light chain for 6H8

<400> SEQUENCE: 6

```
Met Glu Thr Asp Thr Leu Leu Leu Trp Val Leu Leu Leu Trp Val Pro
  1               5                  10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Thr Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Pro
 65                  70                  75                  80

Gly Val Pro Ala Arg Phe Ser Gly Ser Gly Ser Gly Thr Asp Phe Ala
                85                  90                  95

Leu Asn Ile Leu Pro Val Glu Glu Asp Ala Ala Thr Tyr Tyr Cys
                100                 105                 110

Gln His Ser Arg Glu Leu Pro Tyr Thr Phe Gly Gly Gly Thr Lys Leu
            115                 120                 125

Glu Met Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 7
<211> LENGTH: 1544

```
<212> TYPE: DNA
<213> ORGANISM: Artificial Sequence
<220> FEATURE:
<223> OTHER INFORMATION: nucleotide sequence heavy chain for 6H8
<220> FEATURE:
<221> NAME/KEY: misc_feature
<222> LOCATION: '1503'..'1512'..'1515'
<223> OTHER INFORMATION: n represents any nucleotide

<400> SEQUENCE: 7
gaattcggca cgaggcatgg gcaggcttac ttcttcattc ttgctactga ttgtccctgc      60
atatgtcctg tcccaggtta ctctgaaaga gtctggccct gggatattgc agccctccca     120
gaccctcagt ctgacttgtt ctttctctgg gatttcactg accacttctg gtatgggtgt     180
aggctggatt cggcagcctt caggagaggg tctagagtgg ctggcagaca ttttttggga     240
tgacaataag tactataacc cctccctgaa gagccggctc acaatctcca aggatacttc     300
caccaagcag gtattcttca agatcaccag tgtggacact gcagatactg ccacttacta     360
ctgtgttcga gtctactata agaacgacgg gtatttcgat gtctggggcg ctgggaccac     420
ggtcaccgtc tcctcagcca aaacgacacc cccatctgtc tatccactgg cccctggatc     480
tgctgcccaa actaactcca tggtgaccct gggatgcctg gtcaagggct atttccctga     540
gccagtgaca gtgacctgga actctggatc cctgtccagc ggtgtgcaca ccttcccagc     600
tgtcctgcag tctgacctct acactctgag cagctcagtg actgtcccct ccagcacctg     660
gcccagcgag accgtcacct gcaacgttgc ccacccggcc agcagcacca aggtggacaa     720
gaaaattgtg cccagggatt gtggttgtaa gccttgcata tgtacagtcc agaagtatc      780
atctgtcttc atcttccccc caaagcccaa ggatgtgctc accattactc tgactcctaa     840
ggtcacgtgt gttgtggtag acatcagcaa ggatgatccc gaggtccagt tcagctggtt     900
tgtagatgat gtggaggtgc acacagctca gacgcaaccc cgggaggagc agttcaacag     960
cactttccgc tcagtcagtg aacttcccat catgcaccag gactggctca atggcaagga    1020
gttcaaatgc agggtcaaca gtgcagcttt ccctgccccc atcgagaaaa ccatctccaa    1080
aaccaaaggc agaccgaagg ctccacaggt gtacaccatt ccacctccca aggagcagat    1140
ggccaaggat aaagtcagtc tgacctgcat gataacagac ttcttccctg aagacattac    1200
tgtggagtgg cagtggaatg ggcagccagc ggagaactac aagaacactc agcccatcat    1260
ggacacagat ggctcttact tcgtctacag caagctcaat gtgcagaaga gcaactggga    1320
ggcaggaaat actttcacct gctctgtgtt acatgagggc ctgcacaacc accatactga    1380
gaagagcctc tcccactctc tggtaaatg atcccagtgt ccttggagcc ctctggtcct    1440
acaggactct gacacctacc tccacccctc cctgtataaa taaagcaccc agcactgcct    1500
tgngaccctg cnaanaaaaa aaaaaaaaaa aaaaaaaact cgag                     1544

<210> SEQ ID NO 8
<211> LENGTH: 975
<212> TYPE: DNA
<213> ORGANISM: Artificial Sequence
<220> FEATURE:
<223> OTHER INFORMATION: nucleotide sequence light chain for 6H8

<400> SEQUENCE: 8
gaattcggca cgagggagat ggagacagac acactcctgt tatgggtact gctgctctgg      60
gttccaggtt ccactggtga cattgtgctg acacagtctc ctgcttcctt agctgtttct     120
ctggggcaga gggccaccat ctcatgcagg gccagcaaaa gtgtcactac atctgggtat     180
agttttatgc actggtacca acagaaacca ggacagccac ccaaactcct catctatctt     240
```

```
gcatccaacc tagaacctgg ggtccctgcc aggttcagtg gcagtgggtc tgggacagac    300
ttcgccctca acatccttcc tgtggaggag gaggatgctg caacctatta ctgtcagcac    360
agtcgggagc ttccgtacac gttcggaggg gggaccaaac tggaaatgaa acgggctgat    420
gctgcaccaa ctgtatccat cttcccacca tccagtgagc agttaacatc tggaggtgcc    480
tcagtcgtgt gcttcttgaa caacttctac cccaaagaca tcaatgtcaa gtggaagatt    540
gatggcagtg aacgacaaaa tggcgtcctg aacagttgga ctgatcagga cagcaaagac    600
agcacctaca gcatgagcag caccctcacg ttgaccaagg acgagtatga acgacataac    660
agctatacct gtgaggccac tcacaagaca tcaacttcac ccattgtcaa gagcttcaac    720
aggaatgagt gttagagaca aaggtcctga gacgccacca ccagctcccc agctccatcc    780
tatcttccct tctaaggtct tggaggcttc cccacaagcg acctaccact gttgcggtgc    840
tccaaacctc ctccccacct ccttctcctc ctcctcccttt tccttggctt ttatcatgct    900
aatatttgca gaaatattc aataaaagtg agtctttgca cttgaaaaaa aaaaaaaaaa    960
aaaaaaaaac tcgag    975

<210> SEQ ID NO 9
<211> LENGTH: 50
<212> TYPE: DNA
<213> ORGANISM: Artificial Sequence
<220> FEATURE:
<223> OTHER INFORMATION: XhoI sequence

<400> SEQUENCE: 9
gagagagaga gagagagaga actagtctcg agttttttttt ttttttttt    50

<210> SEQ ID NO 10
<211> LENGTH: 20
<212> TYPE: DNA
<213> ORGANISM: Artificial Sequence
<220> FEATURE:
<223> OTHER INFORMATION: G-1U primer

<400> SEQUENCE: 10
gaactctgga tccctgtcca    20

<210> SEQ ID NO 11
<211> LENGTH: 20
<212> TYPE: DNA
<213> ORGANISM: Artificial Sequence
<220> FEATURE:
<223> OTHER INFORMATION: G-1D primer

<400> SEQUENCE: 11
tgcaaggctt acaaccacaa    20

<210> SEQ ID NO 12
<211> LENGTH: 20
<212> TYPE: DNA
<213> ORGANISM: Artificial Sequence
<220> FEATURE:
<223> OTHER INFORMATION: K-1U primer

<400> SEQUENCE: 12
atcttcccac catccagtga    20

<210> SEQ ID NO 13
<211> LENGTH: 19
<212> TYPE: DNA
<213> ORGANISM: Artificial Sequence
```

```
<220> FEATURE:
<223> OTHER INFORMATION: K-1D primer

<400> SEQUENCE: 13
cgtccttggt caacgtgag                                                19

<210> SEQ ID NO 14
<211> LENGTH: 7
<212> TYPE: PRT
<213> ORGANISM: Artificial Sequence
<220> FEATURE:
<223> OTHER INFORMATION: claim 3 -1 (HCDR1)

<400> SEQUENCE: 14

Thr Ser Gly Met Gly Val Gly
  1               5

<210> SEQ ID NO 15
<211> LENGTH: 16
<212> TYPE: PRT
<213> ORGANISM: Artificial Sequence
<220> FEATURE:
<223> OTHER INFORMATION: claim 3 -2 (HCDR2)

<400> SEQUENCE: 15

Asp Ile Phe Trp Asp Asp Asn Lys Tyr Tyr Asn Pro Ser Leu Lys Ser
  1               5                  10                  15

<210> SEQ ID NO 16
<211> LENGTH: 10
<212> TYPE: PRT
<213> ORGANISM: Artificial Sequence
<220> FEATURE:
<223> OTHER INFORMATION: claim 3 -3 (HCDR3)

<400> SEQUENCE: 16

Val Tyr Tyr Lys Asn Asp Gly Tyr Phe Asp
  1               5                  10

<210> SEQ ID NO 17
<211> LENGTH: 8
<212> TYPE: PRT
<213> ORGANISM: Artificial Sequence
<220> FEATURE:
<223> OTHER INFORMATION: claim3 - 4

<400> SEQUENCE: 17

Val Thr Val Pro Ser Ser Thr Trp
  1               5

<210> SEQ ID NO 18
<211> LENGTH: 8
<212> TYPE: PRT
<213> ORGANISM: Artificial Sequence
<220> FEATURE:
<223> OTHER INFORMATION: claim 3 - 5

<400> SEQUENCE: 18

Ser Val Ser Glu Leu Pro Ile Met
  1               5

<210> SEQ ID NO 19
<211> LENGTH: 15
<212> TYPE: PRT
<213> ORGANISM: Artificial Sequence
<220> FEATURE:
<223> OTHER INFORMATION: claim 4 - 1 (LCDR1)
```

```
<400> SEQUENCE: 19

Arg Ala Ser Lys Ser Val Thr Thr Ser Gly Tyr Ser Phe Met His
  1               5                  10                  15

<210> SEQ ID NO 20
<211> LENGTH: 7
<212> TYPE: PRT
<213> ORGANISM: Artificial Sequence
<220> FEATURE:
<223> OTHER INFORMATION: claim 4 - 2 (LCDR2)

<400> SEQUENCE: 20

Leu Ala Ser Asn Leu Glu Pro
  1               5

<210> SEQ ID NO 21
<211> LENGTH: 9
<212> TYPE: PRT
<213> ORGANISM: Artificial Sequence
<220> FEATURE:
<223> OTHER INFORMATION: claim 4 -3 (LCDR3)

<400> SEQUENCE: 21

Gln His Ser Arg Glu Leu Pro Tyr Thr
  1               5

<210> SEQ ID NO 22
<211> LENGTH: 7
<212> TYPE: PRT
<213> ORGANISM: Artificial Sequence
<220> FEATURE:
<223> OTHER INFORMATION: claim 4 - 4

<400> SEQUENCE: 22

Phe Tyr Pro Lys Asp Ile Asn
  1               5

<210> SEQ ID NO 23
<211> LENGTH: 6
<212> TYPE: PRT
<213> ORGANISM: Artificial Sequence
<220> FEATURE:
<223> OTHER INFORMATION: claim 4 - 5

<400> SEQUENCE: 23

Ser Thr Tyr Ser Met Ser
  1               5
```

ANTI-IRC85 MONOCLONAL ANTIBODY; AND COMPOSITION COMPRISING THE SAME FOR PREVENTING AND TREATING TUBERCULOSIS OR ENTERITIS DISEASE; AND THE USE THEREOF

TECHNICAL FIELD

The present invention relates to a new anti-IRC85 monoclonal antibody; the composition comprising the same for preventing and treating tuberculosis or enteritis disease; and the use thereof.

CROSS-REFERENCE TO RELATED APPLICATIONS

This is a U.S. National Stage Application of PCT/KR08/02334 filed on Apr. 24, 2008, and claims foreign priority benefit to parent applications Korean patent application 10-2007-0039791 filed on Apr. 24, 2007 and Korean patent application 10-2008-0037968 filed on Apr. 24, 2008. The entire declaration, oath, specification, disclosure, and drawing figures, and each of them, from said parent patent applications are hereby incorporated herein by reference thereto.

BACKGROUND ART

IRC85 (Z39Ig/CRIg, co-receptor of VSIG4, V-set, Ig-domain-containing 4) consists a signal peptide, an extracellular domain having Ig domain, transmembrane domain, and intracellular domain (Langnasese K., Cloning of Z39Ig, a novel gene with immunoglobulin-like domains located on human chromosome X. *Biochim Biophys Acta.*, pp. 1492-5225, 2000). IRC85 genes were expressed together with typical complement family in macrophages derived from monocytes as well as mainly the fetal tissues, adult lungs and placentas from human (Walker M G., Z39Ig is co-expressed with activated macrophage genes. *Biochim Biophys Acta.*, pp. 1574-3879, 2002). It have been recently established that IRC85 is concerned in removing pathogens opsonized with C3 by phagocytosis, or in preventing the infection into another organ through binding with C3b or IC3b, a by-product of the complement C3 as the receptor of the complement C3 which is highly expressed on Kuffer cells in liver (Helmy K. Y., CRIg; a macrophage complement receptor required for phagocytosis of circulating pathogens, Cell, 124(5): pp. 915-27, 2006).

Therefore, the anti-IRC85 monoclonal antibody specifically binding to IRC85 could become the main target in developing the therapeutic agent to treat various bacterial diseases such as tuberculosis, enteritis disease etc caused by *Tuberculosis, Tubercle bacillus, Yersinia, listeria, Salmonella, Shigella, Legionella, L. monocytogenes* and the like (Melanie Hamon., *Listeria* monocytogens: a multifaceted model, *Nature Reviews microbiology*, pp. 423-434, 2006).

However, there has been not reported or disclosed on the separation of anti-IRC85 monoclonal antibody in any of the above cited literatures. Besides, there has been not reported or disclosed on the anti-bacteria activity of the anti-IRC85 monoclonal antibody against the bacteria infection into cells in any of the above cited literatures.

Therefore, the present inventors have prepared 6H8 hybridoma cell producing novel anti-IRC85 monoclonal antibody specifically binding with IRC85 and found that the antibody showed potent effect in removing the infected/phagocytosed bacteria from THP-1, a monocytic cell that expresses human IRC85 and is infected with *Listeria monocytogenes* or MDR-*tubercle bacillus* to complete the present invention. These and other objects of the present invention will become apparent from the detailed disclosure of the present invention provided hereinafter.

DISCLOSURE

Technical Problem

According to one aspect of the present invention, the present invention provides a new anti-IRC85 monoclonal antibody comprising the sequence with amino acid sequence having SEQ ID No. 5 or more than 90% homology to the amino acid sequence; and the sequence with amino acid sequence having SEQ ID No. 6 or more than 90% homology to the amino acid sequence.

The present invention provides a new anti-IRC85 monoclonal antibody comprising the sequence with the nucleotide sequence having SEQ ID No. 7 or more than 90% homology to the nucleotide sequence; and the sequence with nucleotide sequence having SEQ ID No. 8 or more than 90% homology to the nucleotide sequence.

The present invention provides a novel *Escherichia coli* SOLR/6H8-H cell line (Name of depositary institution: Korean Collection for type Cultures, Date of deposit: Mar. 22, 2007, Accession Number: KCTC11097BP) producing the heavy chain of the above-described new anti-ICR85 antibody.

Also, the present invention provides a novel *Escherichia coli* SOLR/6H8-L cell line (Name of depositary institution: Korean Collection for type Cultures, Date of deposit: Mar. 22, 2007, Accession Number: KCTC11098BP) producing the light chain of the above-described new anti-ICR85 antibody.

The present invention provides a composition comprising a new anti-IRC85 monoclonal antibody as an active ingredient for preventing and treating tuberculosis disease, together with a pharmaceutically acceptable carrier.

Also, the present invention provides a use of new anti-IRC85 monoclonal antibody for the preparation of therapeutic agent for preventing and treating tuberculosis disease in a mammal including human in the need thereof.

The present invention provides an immunotherapeutic method for preventing and treating tuberculosis diseases in a mammal comprising administering to said mammal an effective amount of the above-mentioned new anti-IRC85 monoclonal antibody as an active ingredient, together with a pharmaceutically acceptable carrier thereof.

The present invention provides a composition comprising a new anti IRC85 monoclonal antibody as an active ingredient for preventing and treating enteritis diseases, together with a pharmaceutically acceptable carrier.

Also, the present invention provides a use of new anti-IRC85 monoclonal antibody for the preparation of therapeutic agent for preventing and treating enteritis disease in a mammal including human in the need thereof.

The present invention provides immunotherapeutic method for preventing and treating enteritis disease in a mammal comprising administering to said mammal an effective amount of the above-mentioned new anti-IRC85 monoclonal antibody as an active ingredient, together with a pharmaceutically acceptable carrier thereof.

The present invention provides a health care food comprising a new anti-IRC85 monoclonal antibody as an active ingredient for preventing and improving tuberculosis disease.

The present invention provides a health care food comprising a new anti-IRC85 monoclonal antibody as an active ingredient for preventing and improving enteritis disease.

Technical Solution

Accordingly, it is an object of the present invention to provide a new anti-IRC85 monoclonal antibody comprising the sequence with amino acid sequence having SEQ ID No. 5 or more 90% homology in the amino acid sequence; and the sequence with amino acid sequence having SEQ ID No. 6 or more than 90% homology to the amino acid sequence.

Preferably, the present invention provides a new anti-IRC85 monoclonal antibody consisting of amino acid sequences having SEQ ID No. 5 or SEQ ID No. 6.

In accordance with the other aspect of the present invention, there is also provided a new anti-IRC85 monoclonal antibody comprising the sequence with the nucleotide sequence having SEQ ID No. 7 or more than 90% homology to the nucleotide sequence; and the sequence with nucleotide sequence having SEQ ID No. 8 or more than 90% homology to the nucleotide sequence.

Preferably, the present invention provides a new anti-IRC85 monoclonal antibody coded by the sequences consisting of the nucleotide sequences having SEQ ID No. 7 and SEQ ID No. 8.

More specifically, the term "new anti-IRC85 monoclonal antibody" disclosed herein may comprise the heavy chain comprising at least one polypeptide selected from the group consisting of SEQ ID No. 14 (HCDR1), SEQ ID No. 15 (HCDR2), SEQ ID No. 16 (HCDR3), SEQ ID No. 17 and SEQ ID No. 18, preferably, SEQ ID No. 14 (HCDR1), SEQ ID No. 15 (HCDR2), SEQ ID No. 16 (HCDR3).

Also, the term "new anti-RC85 monoclonal antibody" disclosed herein may comprise the light chain comprising at least one polypeptide selected from the group consisting essentially of SEQ ID No. 19 (LCDR1), SEQ ID No. 20 (LCDR2), SEQ ID No. 21 (LCDR3), SEQ ID No. 22 and SEQ ID No. 23, preferably, SEQ ID No. 19 (LCDR1), SEQ ID No. 20 (LCDR2), SEQ ID No. 21 (LCDR3).

Specially, the term "new anti-IRC85 monoclonal antibody" disclosed herein, shall be understood in the art that the amino acid sequence of the heavy chain includes the other heavy chain variants substituted with the part or sole of the heavy chain amino acid sequence specifically binding to the IRC85 derived from a human, dog, cow, or pig, preferably, human.

Additionally, the term "new anti-IRC85 monoclonal antibody" disclosed herein, shall be understood in the art that the amino acid sequence of the light chain includes the other light chain variants substituted with the part or sole of the heavy chain amino acid sequence specifically binding to the IRC85 derived from a human, dog, cow, or pig, preferably, human.

The present invention also provides a novel *Escherichia coli* SOLR/6H8-H cell (Name of depositary institution: Korean Collection for type Cultures, Date of deposit: Mar. 22, 2007, Accession Number: KCTC11097BP) producing the heavy chain of the above-described new anti-ICR85 antibody.

Also, the present invention provides a new *Escherichia coli* SOLR/6H8-L cell (Name of depositary institution: Korean Collection for type Cultures, Date of deposit: Mar. 22, 2007, Accession Number: KCTC11098BP) producing the light chain of the above-described new anti-ICR85 antibody.

The term "a novel *Escherichia coli* SOLR/6H8-H cell" disclosed herein comprises the cells prepared the method comprising the steps of; preparing cDNA library by isolating mRNA from 6H8-hybridoma cell producing novel anti-IRC85 monoclonal antibody at $1^{st}$ step; searching and detecting the cDNA expressing the light chain of 6H8 antibody by using the constant region of antibody, preferably, CH1 domain of mouse IgG1 cDNA from the cDNA library of the $1^{st}$ step as a probe at the $2^{nd}$ step; and transforming the detected 6H8-H prepared in the $2^{nd}$ step into a plasmid through in vivo excision using by Exassit SOLR system to identify the sequence at the $3^{rd}$ step.

The term "a novel *Escherichia coli* SOLR/6H8-L cell" disclosed herein comprises the cells prepared the method comprising the steps of; preparing cDNA library by isolating mRNA from 6H8-hybridoma cell producing novel anti-IRC85 monoclonal antibody at $1^{st}$ step; searching and detecting the cDNA expressing the light chain of 6H8 antibody by using the constant region of antibody, preferably, CH1 domain of mouse kappa-chain cDNA from the cDNA library of the $1^{st}$ step as a probe at the $2^{nd}$ step; and transforming the detected 6H8-L prepared in the $2^{nd}$ step into a plasmid through in vivo excision using by Exassit SOLR system to identify the sequence at the $3^{rd}$ step.

The present invention provides a pharmaceutical composition comprising a new anti-IRC85 monoclonal antibody as an active ingredient for preventing and treating tuberculosis disease, together with a pharmaceutically acceptable carrier.

Also, the present invention provides a use of new anti-IRC85 monoclonal antibody for the preparation of therapeutic agent for preventing and treating tuberculosis disease caused by in a mammal including human in need thereof.

The present invention provides an immunotherapeutic method for preventing and treating tuberculosis diseases in a mammal comprising administering to said mammal an effective amount of the above-mentioned new anti-IRC85 monoclonal antibody as an active ingredient, together with a pharmaceutically acceptable carrier thereof.

The present invention provides a composition comprising a new anti-IRC85 monoclonal antibody as an active ingredient for preventing and treating enteritis disease, together with a pharmaceutically acceptable carrier.

Also, the present invention provides a use of new anti-IRC85 monoclonal antibody for the preparation of therapeutic agent for preventing and treating enteritis disease in a mammal including human in need thereof.

The present invention provides an immunotherapeutic method for preventing and treating enteritis diseases in a mammal comprising administering to said mammal an effective amount of the above-mentioned new anti-IRC85 monoclonal antibody as an active ingredient, together with a pharmaceutically acceptable carrier thereof.

The present invention provides a health care food comprising a new anti-IRC85 monoclonal antibody as an active ingredient for preventing and improving tuberculosis disease.

The present invention provides a health care food comprising a new anti-IRC85 monoclonal antibody as an active ingredient for preventing and improving enteritis diseases.

Also, the term "tuberculosis disease" disclosed herein comprises MDR-tuberculosis, lung tuberculosis, cystica tuberculosis, bone tuberculosis, guttural tuberculosis, lymph tuberculosis, breast tuberculosis or spinal tuberculosis, preferably, MDR-tuberculosis, which is caused by tuberculosis virulent germ.

Also, the term "enteritis disease" disclosed herein comprises Crohn's disease, colitis, enterocolitis, dysentery, typhoid fever, bromatoxism, chronic colitis, chronic gastroenteritis or acute gastroenteritis, preferably, Crohn's disease, which is caused by enteritis virulent germ.

Also, the term "tuberculosis virulent germ" disclosed herein comprises the germ selected from *Mycobacterium tuberculosis, tubercle bacillus*, or *Legionella*, specifically, *tubercle bacillus*.

Also, the term "enteritis virulent germ" disclosed herein comprises the germ belonged to the genus selected from *Yersina, Listeria, Salmonella*, or *Shigella*, specifically, *Listeria* or *Salmonella*.

Hereinafter, the present invention is described in detail.

Specifically, the inventive anti-IRC85 monoclonal antibody of the present invention may be prepared by the method well-known in the art (Ed Harlow, Antibodies; A Laboratory manual, Cold Sproing Harbor laboratory press, pp 196-218), and exemplary method is shown as follows: Present invention provides a method for preparing the inventive anti-IRC85 monoclonal antibody by the method comprising the steps consisting of: injecting IRC85-expressing cell line (1-1C2) BALB/c mouse four times for every other weeks to immunization at the $1^{st}$ step; isolating B lymphocyte from the spleen of the immunized mouse at the $2^{nd}$ step; mixing the B lymphocyte with myeloma cell such as Sp2/0-Ag14 with the mixed ratio of 3:1 to fuse in DMSO medium comprising 50% PEG for 1 minute and washing with DMEM medium supplemented with high-concentrated sugar which was diluted with 50% PEG at the $3^{rd}$ step; suspending the fused cells in HAT medium to select the hybridoma cells fused with only B lymphocyte and Sp2/0-Ag14 at the $4^{th}$ step; and selecting 6H8 hybridoma cell producing new anti-ICR85 monoclonal antibody from the hybridoma cells.

Accordingly, the present invention provides a composition comprising a new anti-IRC85 monoclonal antibody prepared by the above-described method as an active ingredient for preventing and treating enteritis disease, together with a pharmaceutically acceptable carrier.

Also, the present invention provides a use of new anti-IRC85 monoclonal antibody prepared by the above-described method for the preparation of therapeutic agent for preventing and treating enteritis disease in a mammal including human in need thereof.

The present invention provides an immunotherapeutic method for preventing and treating enteritis diseases in a mammal comprising administering to said mammal an effective amount of the above-mentioned new anti-IRC85 monoclonal antibody prepared by the above-described method as an active ingredient, together with a pharmaceutically acceptable carrier thereof.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The inventive composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing inventive composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), suppository, or sterile injectable preparation (solution, suspension, emulsion).

The inventive composition of the present invention in pharmaceutical dosage forms may be used in the form of their pharmaceutically acceptable salts, and also may be used alone or in appropriate association, as well as in combination with other pharmaceutically active compounds.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 0.0001 to 100 mg/kg, preferably, 0.001 to 10 mg/kg by weight/day of the inventive composition of the present invention. The dose may be administered in a single or multiple doses per day.

The inventive composition can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

In accordance with one aspect of the present invention, there provided a health care food comprising the above described antibody preventing and improving tuberculosis disease or enteritis diseases.

Above described antibody therein can be added to food, additive or beverage for prevention and improvement of purposed target diseases. For the purpose of preventing and improving purposed target diseases, wherein, the amount of above described composition in food or beverage may generally range from about of total weight of food for the health beverage composition and 0.02 to 10 g, preferably 0.3 to 1 g on the ratio of 100 ml of the health beverage composition.

Providing that the health beverage composition of present invention contains above described composition as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Examples of addable food comprising aforementioned composition therein are various food, beverage, gum, vitamin complex, health improving food and the like.

It will be apparent to those skilled in the art that various modifications and variations can be made in the compositions, use and preparations of the present invention without departing from the spirit or scope of the invention.

Advantageous Effects

Inventive anti-IRC85 monoclonal antibody of present invention showed potent anti-bacterial activity against *Listeria mnocytogenes* and *Tubercle bacillus*, therefore it can be useful as a composition for treating and preventing tuberculosis disease and enteritis disease.

DESCRIPTION OF DRAWINGS

The above and other objects, features and other advantages of the present invention will more clearly understood from the following detailed description taken in conjunction with the accompanying drawings, in which;

FIG. 1 represents the vector-map in IRC85/pcDNA3.1;

FIG. 2 represents the expression of IRC85 cell;

BEST MODE

Figure 3:
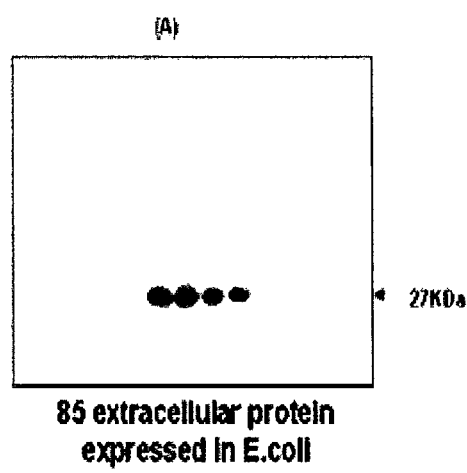
FIG. 3 presents the expression and purification of IRC85 protein from *E. Coli*.

It will be apparent to those skilled in the art that various modifications and variations can be made in the compositions, use and preparations of the present invention without departing from the spirit or scope of the invention.

MODE FOR INVENTION

The present invention is more specifically explained by the following examples. However, it should be understood that the present invention is not limited to these examples in any manner.

Example 1

Preparation of Hela Cell Expressing IRC85

1-1. IRC85 Cloning Using pcDNA3.1

To express IRC85 in animal cells, pcDNA3.1 (Invitrogen Co. Ltd., See FIG. 1) was used and full-length of IRC85 was prepared to use by PCR for cloning vectors. The primers of IRC85 was shown in following Table 1.

TABLE 1

| Gene | | Primer Sequence |
|---|---|---|
| IRC85 | sense: SEQ ID No. 1 | 5'-CGGGATCCGAATTCGGTACCCGTCC CATCCTGGAAGTGCCAGAG-3' |
| IRC85 | anti-sense: SEQ ID No. 2 | 5'-CGGGATCCGAATTCGGTACGATGAA GTTGCCATTCTGCCTGCC-3' |

2 μl of template, 2 μl of 2.5 mM dNTP, 1 μl of 10 pM sense/anti-sense primer, 5 μl of 10×PCR buffer (100 mM Tris-HCl, 500 mM CaCl2, 15 mM Magnesium Chloride, pH 8.3), and 0.5 μl of Tact polymerase (1 U/ml, Roche) were mixed and the final volume of the solution was adjusted to a deionized water to 50 μl to perform PCR reaction by PCR apparatus (Perkin-Elmer, GeneAmp PCR system 2400).

PCR reaction was performed as follows: 1 cycle for 5 mins at 94° C.; 8 cycles for 30 sec at 94° C., for 30 sec at 50° C., for 45 sec at 72° C.; 30 cycles for 30 sec at 94° C., 30 sec for 65° C., 45 sec at 72° C.; 1 cycle for 5 mins at 72° C.

pcDNA 3.1 and PCR byproduct were excised by restriction enzyme BamH I/Not I, and the excised DNA was confirmed by electrophoresis developed with 1% agarose gel to extract using by Gel extraction kit (QIAGEN, QIAquick Gel extraction kit, Cat#28706). The extracted vector and PCR product was mixed with the ratio of 1:3, and 10 μl of 2× ligation buffer, and 1 μl of T4 DNA ligase (100 U/ml) were added thereto to adjust the final concentration 20 μl. The synthetic reaction was performed at room temperature for 2 hours, and ligate was mixed with 200 μl of DH5 α competent cell thoroughly to be left alone in iced water for 45 mins and then heated at 42° C. for 90 sec. The reaction solution was left alone in iced water for 5 mins and 500 μl of 1×LB medium was added thereto to incubate at 37° C. for 60 mins. After the incubation, the solution was centrifuged with the speed of 14000 rpm for 10 sec and 100 μl of supernatant was collected. The cell pellet was suspended in the supernatant and the cell was cultured for 16 hours by spreading onto 1×LB/Amp (100 μg/ml) plate to transformation. The colony grown in Ampicillin selection broth was inoculated into LB/Amp broth to incubate and isolate plasmid DNA.

1-2. Isolation of Plasmid DNA

Plasmid DNA was extracted from the inoculated bacteria in Example 1-1 according to Alkaline lysis method. The bacteria were collected and suspended in 100 μl of mixture solution I (50 mM glucose, 25 mM Tris-HCl, 10 mM EDTA, pH 8.0). 200 μl of solution II (0.2 N NaCl, 1% SDS) was added to give rise to soft inverting and left alone for 5 mins at room temperature. 5 mins after the incubation, solution DI (3 M Potassium acetate, glacial acetic acid) was added thereto to be left alone in ice for 5 mins, and centrifuged with the speed of 14000 rpm for 10 mins. The supernatant was transferred to new tube, and two fold volume of ethanol was added thereto to centrifuge again with the speed of 14000 rpm for 10 mins. After the centrifugation, the supernatant was discarded, washed with 1 ml of 70% ethanol, and the plasmid DNA was dried in the air to dissolve in deionized solution. 3 μl of the prepared DNA was excised by restriction enzyme BamH I/Not I for 2 hours at 37° C. to perform electrophoresis on 1% agarose gel for 2 hours and confirm the insertion to cloning.

Example 2

Transfection of IRC85/pcDNA3.1 into Hela Cell 2-1. Culture of Hela Cell

Hela cell (ATCC) was cultured in high glucose DMEM (Dulbeccos Modified Eagle Medium, GIBCO/BRL) supplemented with 10% FBS (fetal bovine serum), penicillin (100 IU/ml) and streptomycin (100 μl/ml) at 37° C. in 5% $CO_2$ incubator.

2-2. Transfection into Hela Cell

The transfection into HeLa cell was performed according to calcium phosphate method (Hohn E. Coligan., Short Protocols in Immunology, pp. 14-2~14-5, 2005).

One day before the transfection, $5\times10^5$ cells were plated onto 6-well plate and the cells were replaced with new broth one hour before transfection. For transfection, 10 μg of DNA was added to 84.5 μl of DDW and mixed with 12.5 μl of 2.5 M calcium chloride. Identical volume of 2×HBS (280 mM sodium chloride, 10 mM potassium chloride, 1.5 mM disodium hydrogen phosphate, 2 mM dextrose, 50 mM HEPES, pH 7.05) was added thereto dropwisely with vortexing and the mixture was left alone for 20 mins at room temperature to transfer into each well. 6 hours after transfection, cells were washed with PBS and the medium was replaced with new medium.

2-3. Selection of Transfectant 48 hours after transfection in Example 2-2, 200 μg/ml of neomycin was treated thereto. The day after the treatment, dead cells were removed and the transfectant were further cultured with inconstant treatment with neomycin. The cell lines were performed to FACS analysis using anti-plague antibody to confirm whether the IRC85 was expressed or not. The data of FACS analysis for approximately 100 cells was shown in FIG. 2. As shown in FIG. 2, it has been confirmed that the expression of IRC85 was expressed in 3 clones, and 1-1C2 clone showed the most potent expression among them. Afterwards, 1-1C2 was used in immunization (See FIG. 2).

Example 3

Preparation of IRC85-His Recombinant Protein 3-1. Cloning of IRC85 Extracellular Domain To clone of IRC85 extracellular domain, primers were prepared and the sequence of the primers was shown in Table 2.

The PCR products prepared by using IRC85 His-sense and IRC85 His-anti-sense as shown in Table 2, was excised with BamH I/Hind III and performed to ligation to with pET21-(a)+excised with same restriction enzyme. The transformation and plasmid extraction were followed to cloning.

TABLE 2

| Recombinant Protein | | Primer Sequence |
|---|---|---|
| IRC85 | His-sense: SEQ ID No. 3 | 5'-CGCGGATCCCAGCAGGCAAAGTACC AG-3' |
| IRC85 | His-anti-sense: SEQ ID No. 4 | 5'-GACAAGCTTCAGGCTCTTTCCTGGC C-3' |

3-2. Expression and Isolation of IRC85-His Recombinant Protein pET21-(a)+/85ext prepared in Example 3-1 was transformed into BL21 (DE3) *E. coli* and the protein was expressed using 0.1 mM IPTG. The expressed recombinant protein was isolated by using by Ni-NTA resin since it comprises 6×His tag. It expressed 26 KDa by comprising 25 kDa polypeptide expressed from the 700 by DNA located in IRC85 extracellular domain and 66 Da His tag. FIG. 3 showed that the practically isolated IRC85 using Ni-NTA resin, has 27 KDa with low level of expression since IRC85 extracellular domain mainly consists of hydrophobic amino acids (See FIG. 3). The isolated protein was used as an antigen for ELISA screening during the preparation of monoclonal antibody.

Example 4

Preparation of the Monoclonal Antibody Against Anti-IRC85

4-1. Mouse Immunization 1-1C2 cell line, a cell line expressing IRC85 (IRC: Immunomodulation Research Center) was injected into 4-weeks BALB/c mouse for 2 weeks in a dose of $2\times10^7$ cells/mouse four times. 3 days after the $4^{th}$ injection, the mouse tail was cut to collect blood and the titer of antibody was determined. ELISA was performed using by IRC85-His protein and the dilution less than 1/100000 of the serum showed significance. Fusion was performed by using the mouse.

4-2. The Culture of Myeloma Cell

Sp2/0-Ag14 cell line (ATCC) was incubated in high glucose DMEM (Dulbeccos Modified Eagle Medium, GIBCO/BRL) supplemented with 10% fetal bovine serum, penicillin (100 IU/ml) containing streptomycin (100 μl/ml) at 37° C., in 5% $CO_2$ incubator.

4-3. Fusion of B Lymphocyte with Sp2/0-Ag14

3 days after the final injection into immunized BALB/c mouse in Example 4-1, the spleen was delivered to prepare a spleen lymphocyte using by injector. The cells were transferred to 50 ml of conical tube and the tube was full with serum-free DMEM medium to centrifuge for 5 mins with the speed of 1000 rpm. After twice washing, the supernatant was discarded and RBC was removed according to hypotonic lysis method. The tube was full with medium and centrifuged. During the final washing step, Sp2/0-Ag14 myeloma cells were collected. The spleen lymphocyte and SP2/0 myeloma cells were suspended again in medium, and the number of cells was counted using by hematocytometer. The mixture of the spleen lymphocyte and Sp2/0 myeloma cells (3:1) in 50 ml of conical tube was centrifuged with speed of 800 rpm for 5 mins. 1 ml of 50% PEG (polyethylene-glycol 3000 in DMSO, Sigma Co.) was added thereto with vortexing to perform fusion, and the added PEG solution was washed by following diluting steps with high glucose DMEM: twice for 1 ml/min, twice for 5 ml/min, and twice for 10 ml/min. After further washing steps for two times, the fused cells were suspended in HAT-containing medium and distributed to 96-well plates for selection of fused cells.

4-4. ELISA (Enzyme-Linked Immuno Sorbent Assay) Screening

IRC85-His protein purified from pET21-(a)+/85ext in Example 3-2 was diluted with coating buffer (0.03 M sodium carbonate, 0.068 M sodium bicarbonate, pH 9.4) to the final concentration be 1 μg/ml, and distributed onto ELISA-96 well plates by 100 μl/well to coat at 4° C. for overnight. The supernatant was removed and 3% skim milk was distributed by 100 µl to incubate at 37° C. for 1 hour. PBS-T (0.05% Tween-20 in PBS) was distributed onto the plates by 200 µl and washed three times. The supernatant of fused cells was distributed onto each cell by 100 µl to react for 2 hours at room temperature. PBS-T was added thereto by 200 µl and the plates were washed four times. The diluted anti-mouse IgG-AP with PBS-T to 1:5000, was distributed onto the plates by 100 µl/well to incubate at 37° C. for one hour. The plates were washed with PBS-T three times and 1 mg/ml of phosphatase substrate (Sigma Co., 104-0) dissolved in carbonate buffer (0.1 M sodium carbonate, 1 mM magnesium chloride, pH 9.8) was distributed onto each well by 50 µl/well and incubated at 37° C. for 30 mins in the shadow. After the reaction, the absorbance was determined at $OD_{405}$ nm to select positive clone-containing wells. Through the $1^{st}$ screening, many clones were selected, transferred to 24-well plates to incubate and mono cell cloning was performed several times to obtain purposed monoclonal antibody.

Experimental Example 1

Selection of Monoclonal Antibody Using FACs Analysis

Further FACS was performed using by ELISA-screened clone. 1-1C2 cells were washed twice with FACS buffer (PBS+0.1% BSA) and the culture medium of each hybridoma was treated thereto by 200 µl/well to incubate for 30 mins at 4° C. and washed with FACS buffer twice. The washed cells were stained again with anti-mouse IgG-FITC and the result was determined by FACScan (Becton Dickinson, FACScalibar, Immunocytometry System 2350).

Figure 4:
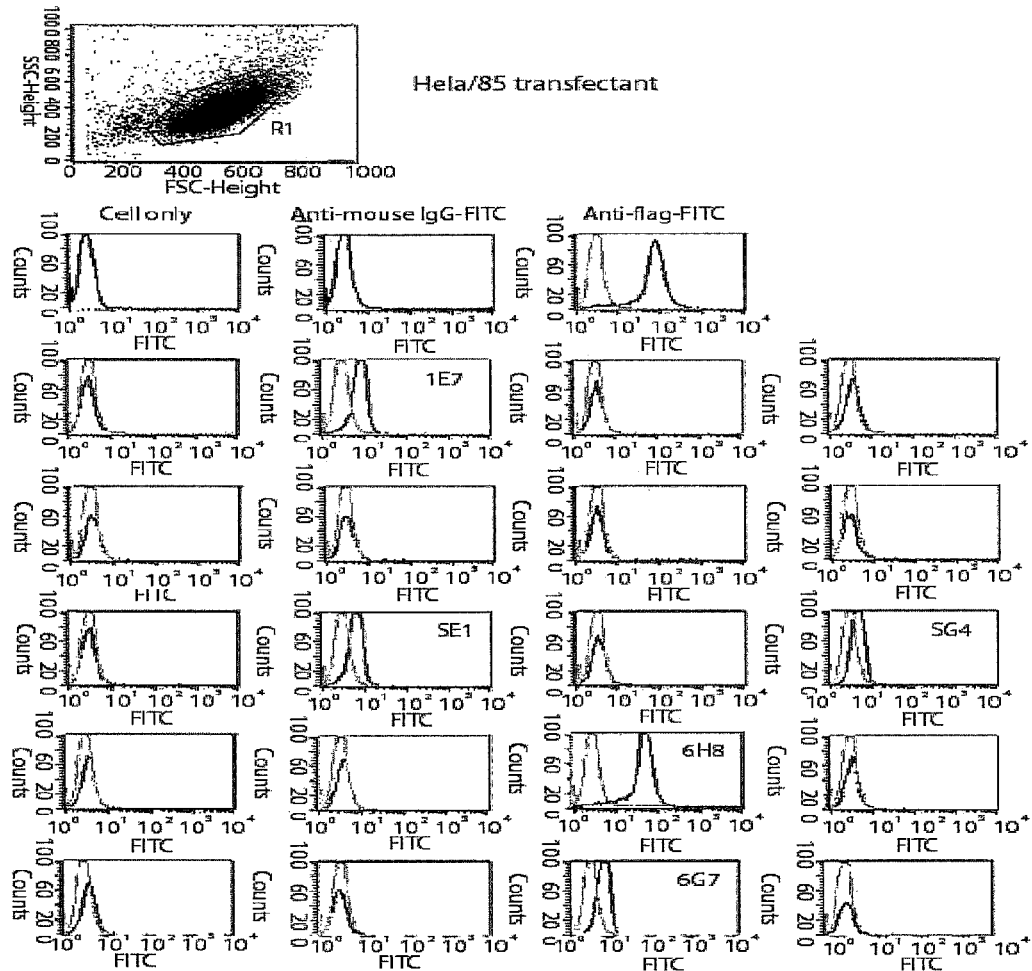
FIG. 4 presents the FACS analysis of inventive monoclonal antibody.

At the result, as shown in FIG. 4, it has been confirmed that among the hybridized clones, anti-IRC85 monoclonal antibody 6H8 (designated as "6H8" hereinafter) expressed as amino acid sequence of SEQ ID No. 5 and 6, or encoded thereof by nucleotide sequences of SEQ ID No. 7 and 8 showed most potent binding activity (See FIG. 4).

Experimental Example 2

Anti-Bacterial Activity of Anti-IRC85 Monoclonal Antibody (6H8)

2-1. Expression of IRC85 onto the Surface of THP-1 Cell

To determine whether IRC85 could be expressed on the surface of THP-1 cell or not, FITC-binding anti-IRC85 monoclonal antibody was prepared according to the standard manual using FITC (Cat#46110, Pierce). Human Ab antibody was added to the collected cells to block the Fc receptor and the cell was stained with FITC-binding anti-human IRC85 monoclonal antibody for 30 mins to perform flow cytometry analysis (Hohn E., Short Protocols in Immunology, pp. 5-23, 2005).

To determine whether the expression of IRC85 are related to the cell activation or not in monocyte cells, LPS was added to THP-1 cell (human monocyte) and the cells were collected by every hour to determine the expression of human IRC85.

Figure 5:
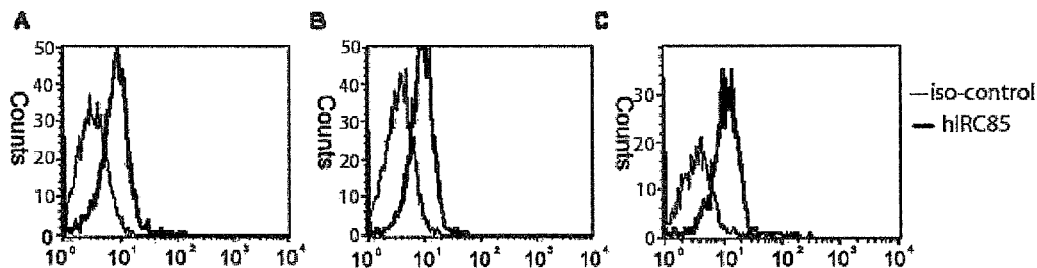
FIG. 5 depicts the expression of IRC85 in THP-1 cell.

At the result, as shown in FIG. 5, it has been confirmed that the expression of human IRC85 had been rather increased with time than that at initial time however the increasing tendency has not maintained (See FIG. 5).

2-2. Bactericidal Effect of Anti-IRC85 Antibody on *L. Monocytogenes*

To determine the anti-human IRC85 monoclonal antibody (6H8) has bactericidal effect in THP-1 cell infected with *L. monocytogenes* or not, the bacterial removing ratio of the antibody in bacteria infected cells was determined as follows (Ouadrhiri Y., Mechanism of the Intracellular Killing and Modulation of Antibiotic Susceptibility of *Listeria monocytogenesin* THP-1 Macrophages Activated by Gamma Interferon. Antimicrob Agents Chemother., 43(5), pp. 1242-1251, 1999).

THP-1 cell (ATCC, $4\times10^5$ cells/nil) was induced to be infected with 10 WI of *L. monocytogenes* (ATCC 19111, KTCC) at 37° C. for 1 hour. After the phagocytosis, the cell was centrifuged for 10 mins with speed of 600×g, washed with PBS and the steps were repeated four times to remove only the cells which are not phagocytized. 300 µg/ml of ampicillin was added thereto to incubate at 37° C. for 15 mins and the adhered bacteria was removed. The infected cell was distributed to 24-well plates and treated with anti-IRC85 or mouse IgG antibody to collect the cells at every hour. The cell was once washed with PBS, dissolved in distilled water and performed to plating on BHIB (brain heart infusion broth; Difco Laboratories, Detroit, Mich.) medium according to dilution method. More than 12 hours after the incubation at 37° C., the values of CFU (colony forming unit) and removal ratio were determined by counting the number of colony observed.

Additionally, to examine the bacteriocidal effect of anti-IRC85 antibody according to the activated status of THP-1 cell, the cell was incubated with LPS for 24 hours to induce the cell-activation of THP-1 cell and the THP-1 cell cultured in LPS-absent medium was used as a control. The removal ratio of THP-1 cell due to anti-IRC85 antibody on *L. monocytogenes* was determined through the similar test using by two kinds of cells.

Figure 6:
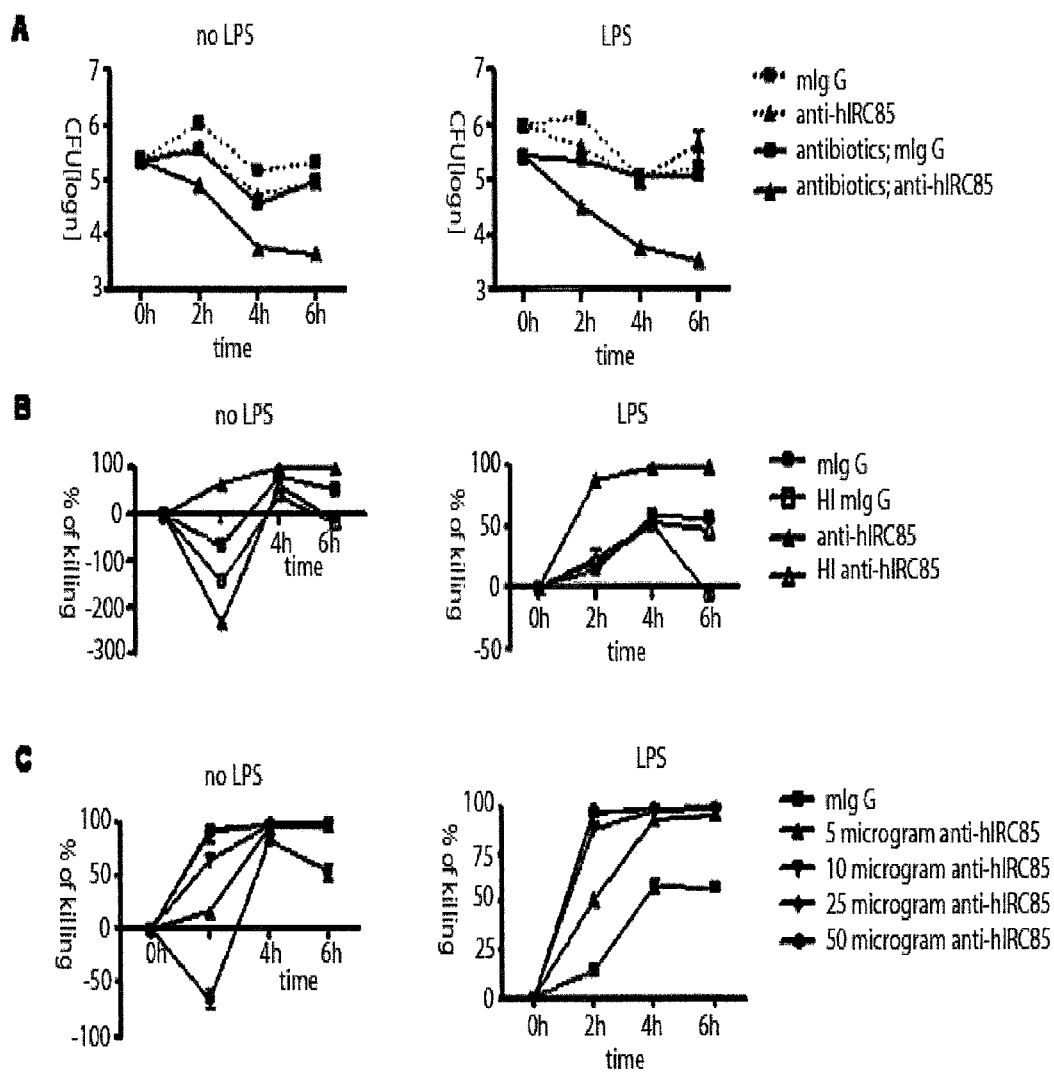
FIG. 6 presents the removal rate of anti-human IRC85 monoclonal antibody against *Listeria monocytogenes* according to various concentrations.
Figure 7:
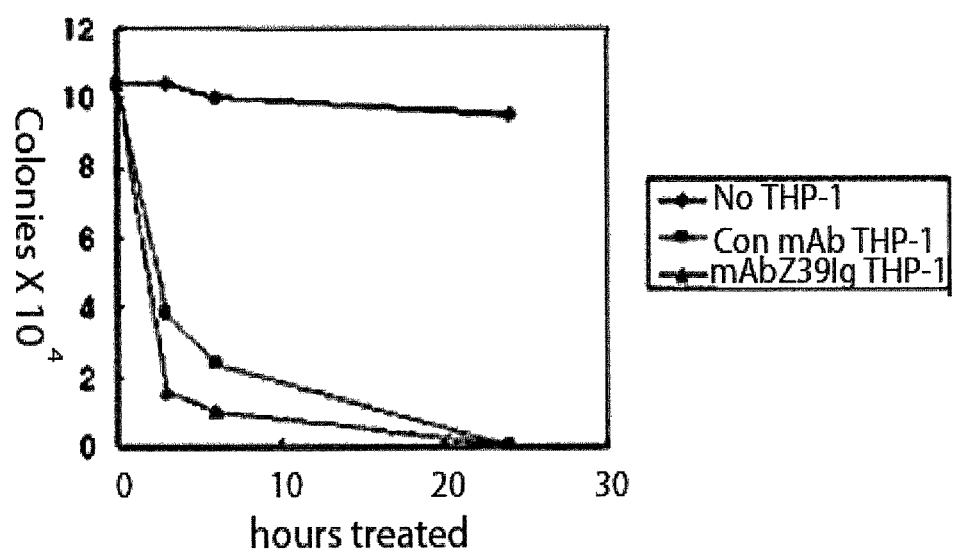
FIG. 7 depicts the removal rate of anti-human IRC85 monoclonal antibody against MDR (multi-drug resistance) tuberculosis according to various concentrations.

At the result, as shown in FIG. 6A, it has been confirmed that both of the activated cell and inactivated cell showed similarly reduced number of bacteria due to anti-IRC antibody (See FIG. 6A). Accordingly, the number of bacteria was reduced where the cell was treated with anti-IRC85 antibody regardless of the activation of THP-1 cell.

Additionally, to confirm that the removing effect on *L. monocytogenes* has been due to the specific activity to the antibody, the similar test to the above-mentioned method excepting adopting normal antibody and heated antibody to be treated to bacteria-infected cells, were performed.

At the result, as shown in FIG. 6B, both of the heated isotype antibody and anti-human IRC85 monoclonal antibody showed reduced removal ratio of bacteria (See FIG. 6B), which confirmed that the bacteriocidal activity was significantly reduced in case the antibody had been heated to induce the inactivation of activity.

Additionally, to examine the removal effect according to the concentration of the antibody, the similar test to the above-mentioned method excepting adopting various concentration of antibody to be treated to bacteria-infected cells, were performed.

At the result, as shown in FIG. 6C, the bactericidal activity of antibody was increased in a dose dependent manner. It has reached to almost 100% when treated with the concentration of more than 10 µg antibody for two hours and at four hours after the test, to 100% at overall concentrations (See FIG. 6C). Through the result, the removal speed and removal rate of *Listeria monocytogenes* had been increased where the THP-1 cell infected with *Listeria monocytogenes* was treated anti-IRC85 monoclonal antibody (6H8) compared with that in control group.

2-3. Removal Effect of Anti-IRC85 Monoclonal Antibody on MDR (Multi-Drug Resistance) *Tubercle Bacillus*

To determine the bacteriocidal effect of anti-IRC85 monoclonal antibody on the THP-1 cell infected with MDR (multi-drug resistance) *tubercle bacillus*, provided by ITRC (International Tuberculosis TB Research Center), the removal activity of bacteria was determined by treating the bacteria-infected cell with the antibody according to following procedure (Ouadrhiri Y., *Mechanism of the Intracellular Killing and Modulation of Antibiotic Susceptibility of Listeria monocytogenesin THP-*1 *Macrophages Activated by Gamma Interferon. Antimicrob Agents Chemother.,* 43(5), pp. 1242-1251, 1999).

THP-1 cell (ATCC, $4\times10^5$ cells/ml) was infected with 10 MOI of MDR *tubercle bacillus* at 37° C. for 1 hour. After the end of phagocytosis, the cell was centrifuged with speed of 600×g for 10 mins to collect the infected cells, washed with PBS and the steps were repeated three times to remove the cell which had not been phagocytosized. The cell was treated with 5 μg/ml of mIgG or anti-IRC85 antibody, incubated at 37° C., and the cell was collected at every hour to form colony by plate incubating on H9 agar plate. The removal ratio of MDR *tubercle bacillus* due to the anti-IRC85 monoclonal antibody was determined.

At the result, as shown in FIG. 7, the THP-1 cell infected with MDR *tubercle bacillus* was disappeared with and completely disappeared at 24 hours after the infection. The removal speed of MDR *tubercle bacillus* where the antibody was treated, was faster and about 90% the bacteria disappeared three hours after the infection, which results confirmed that the inventive antibody (6H8) showed potent anti-bacterial activity of MDR *tubercle bacillus* (See FIG. 7).

Experimental Example 3

Cloning of Anti-IRC85 Monoclonal Antibody (6H8) Prepared from Mouse 3-1. Extraction of mRNA from 6H8-Producing Cell Line (6H8 Hybridoma)

Total RNA was extracted from the cell line producing $2\times10^8$ 6H8 according to the instruction manual (Easy-Blue Isolation Kit, Intron Co.).

The cell pellet was treated with Easy-Blue Isolation Kit reagent (Easy-Blue Isolation Kit, Intron Co.) and extracted with phenol/chloroform once. The supernatant was treated with isopropanol to precipitate RNA, washed with 75% ethanol twice and dissolve in distilled water treated with DEPC (Sigma Co.) to obtain total RNA. The extraction of mRNA from the total RNA was isolated and purified by using Dynalbeads mRNA purification kit (DYNAL Co.).

3-2. Preparation of cDNA Library Producing 6H8-Producing Cell Line (6H8 Hybrioma)

To prepare cDNA library from 6H8-producing cell line, ZAP-cDNA synthesis kit (Stratagene Co. Ltd) and ZAP-cDNA Gigapack III Gold Cloning Kit Stratagene Co. Ltd) were used in the experiment.

The mixture of 5 μg of mRNA prepared in Experimental Example 3-1, 2.8 μg of linker primer having XhoI recognition sequence (SEQ ID No. 9; 5'-gagagagagagagagagagaactagtctcgagttttttttttttttttt-3'), RNaseH reverse transcriptase (40 U, #200450, Stratagene Co. Ltd), methyl nucleotide mixture (1.25 mM) and RNase inhibitor (40 U, #200450, Stratagene Co. Ltd) was reacted at 37° C. for 1 hour to synthesize the primary strand. RNase H (3 U) and DNA polymerase I (99 U, #200450, Stratagene Co. Ltd) were reacted at 16° C. for 2.5 hours to synthesize the secondary strand. After the reaction, the strands were extracted with phenol/chloroform, concentrated with ethanol, washed with 70% ethanol and the precipitate was dissolved in water. The protein was dissolved in water and removed by using Ultrafree-Probind filter (Sigma Co. Ltd). 3 and 5 terminal end were blunt-ended by using Klenow fragment and dNTP and the protein was removed by using Ultrafree-Probind filter (Sigma Co. Ltd). 2 mM rATP and T4 DNA ligase (2 U) were added thereto to incubate at 4° C. for 12 hours and EcoRI enzyme was inactivated by heating at 70° C. for 30 mins. 2 mM rATP and T4 polynucleotide kinase (10 U) were added thereto to react at 37° C. for 30 mins. The terminal end of EcoRI was to form kinase by heating at 70° C. for 30 mins and cut by XhoI. The protein was removed by using Ultrafree-Probind filter (Sigma Co. Ltd) to obtain cDNA and the amount of cDNA was determined according to ethidium bromide plate analysis. The mixture of 125 μg of Uni-ZAP XR vector (#200450, Stratagene Co. Ltd), rATP (1 mM) and T4 DNA ligase (2 U) was added to 100 ng of cDNA to react at 12° C. for 12 hours. When the packaging extract (#200450, Stratagene Co. Ltd) being kept at 80° C. started to melt, 2 μl of the linked DNA was added thereto and mixed together with pippet to react at room temperature for 2 hours. SM buffer solution (100 mM sodium chloride, 10 mM magnesium sulfate, 50 mM Tris-HCl pH 7.5, 0.01% gelatin) was added thereto, mixed with 20 μl of chloroform, centrifuged to supernatant and the supernatant was transferred to new tube.

*E Coli* XL-1 blue MRF' (Stratagene Co. Ltd) was used as a host cell, and the colony obtained by spreading on LB/tetracycline (50 μg/ml) plate, was inoculated to LB medium containing 10 mM magnesium sulfate and 0.2% maltose. The cell was bred with stirring at the speed of 200 rpm at 37° C. on condition that $OD_{600}$ had not exceeded 1.0. The culture medium was centrifuged at the speed of 500×g at 10 mins to remove the medium, and diluted by adding 10 mM magnesium sulfate to the cell pellet to the extent that $OD_{600}$ had reached to 0.5. The host cell was stored at 4° C. to use for 48 hours.

1 μl of 1/10 fold diluted packaged reaction was added to 200 μl of host cell to adhere at 37° C. for 15 mins. 3 ml of top agar cooled to 48° C. was added thereto with vortexing and poured on the preheated LB agar plate immediately to grow at 37° C. for 10 hours. The number of plague (pfu/ml) was counted and cDNA library having a size of $3.8\times10^5$ pfu was obtained.

3-3. Screening of Heavy Chain Gene and Kappa Chain Gene

The transformed cell line obtained from Experimental Example 3-2, was plated on the plate (100 mm) in order to form about 200-300 plagues, and transferred to nylon membrane to form UV crosslinking. The hydridization using by the membrane was performed. The invariant fragment cloned by PCR was used as the probe for screening the kappa chain of heavy chain and light chain. In detail, G-1U: 5'-gaactctggatccctgtcca-3' of SEQ ID No. 10 and G-1D: 5'-tgcaaggcttacaaccacaa-3' of SEQ ID No. 11 were used as PCR primer for obtaining a heavy chain probe to prepare the CH1 domain of mouse IgG1 cDNA and 200 by PCR product was obtained to use as a probe. K-1U: 5'-atcttcccaccatccagtga-3' of SEQ ID No. 12 and K-1D: 5'-cgtccttggtcaacgtgag-3' of SEQ ID No. 13 were used as PCR primer for obtaining a light chain probe to prepare the CH1 domain of mouse kappa chain cDNA, 200 by PCR product was obtained to use as a probe. The hydridization was performed by using ECL direct nucleic acid labelling and detection kit (#RPN3000, Amersham), and the clone prepared thereby was transformed to plasmid to confirm the sequence through in vivo excision using Exassit/SOLR system. The amino acid sequence and nucleotide sequence of the heavy chain gene and kappa chain was shown in following Table 3.

TABLE 3

| Antibody | Chain | Sequence | |
|---|---|---|---|
| 6H8 | Heavy chain | amino acid sequence (464 a.a.): SEQ ID No. 5 | MGRLTSSFLLLIVPAYVLSQVTLKESGPGILQPSQTLSLTCSFSGISL TTSGMGVGWIRQPSGEGLEWLADIFWDDNKYYNPSLKSRLTISKDTST KQVFFKITSVDTADTATYYCVRVYYKNDGYFDVWGAGTTVTVSSAKTT PPSVYPLAPGSAAQTNSMVTLGCLVKGYFPEPVTVTWNSGSLSSGVHT FPAVLQSDLYTLSSSVTVPSSTWPSETVTCNVAHPASSTKVDKKIVPR DCGCKPCICTVPEVSSVFIFPPKPKDVLTITLTPKVTCVVVDISKDDP EVQFSWFVDDVEVHTAQTQPREEQFNSTFRSVSELPIMHQDWLNGKEF KCRVNSAAFPAPIEKTISKTKGRPKAPQVYTIPPPKEQMAKDKVSLTC MITDFFPEDITVEWQWNGQPAENYKNTQPIMDTDGSYFVYSKLNVQKS NWEAGNTFTCSVLHEGLHNHHTEKSLSHSPGK |
| 6H8 | Light chain | amino acid sequence (238 a.a.): SEQ ID No. 6 | METDTLLLWVLLLWVPGSTGDIVLTQSPASLAVSLGQRATISCRASKS VTTSGYSFMHWYQQKPGQPPKLLIYLASNLEPGVPARFSGSGSGTDFA LNILPVEEEDAATYYCQHSRELPYTFGGGTKLEMKRADAAPTVSIFPP SSEQLTSGGASVVCFLNNFYPKDINVKWKIDGSERQNGVLNSWTDQDS KDSTYSMSSTLTLTKDEYERHNSYTCEATHKTSTSPIVKSFNRNEC |
| 6H8 | Heavy chain | nucleotide sequence: SEQ ID No. 7 | TTCAAATGCAGGGTCAACAGTGCAGCTTTCCCTGCCCCCATCGAGAAA ACCATCTCCAAAACCAAAGGCAGACCGAAGGCTCCACAGGTGTACACC ATTCCACCTCCCAAGGAGCAGATGGCCAAGGATAAAGTCAGTCTGACC TGCATGATAACAGACTTCTTCCCTGAAGACATTACTGTGGAGTGGCAG TGGAATGGGCAGCCAGCGGAGAACTACAAGAACACTCAGCCCATCATG GACACAGATGGCTCTTACTTCGTCTACAGCAAGCTCAATGTGCAGAAG AGCAACTGGGAGGCAGGAAATACTTTCACCTGCTCTGTGTTACATGAG GGCCTGCACAACCACCATACTGAGAAGAGCCTCTCCCACTCTCCTGGT AAATGATCCCAGTGTCCTTGGAGCCCTCTGGTCCTACAGGACTCTGAC ACCTACCTCCACCCCTCCCTGTATAAATAAAGCACCCAGCACTGCCTT GNGACCCTGCNAANAAAAAAAAAAAAAAAAAAAAAAACTCGAG |
| 6H8 | Light chain | nucleotide sequence: SEQ ID No. 8 | GAATTCGGCACGAGGGAGATGGAGACAGACACACTCCTGTTATGGGTACTG CTGCTCTGGGTTCCAGGTTCCACTGGTGACATTGTGCTGACACAGTCTCCT GCTTCCTTAGCTGTTTCTCTGGGGCAGAGGGCCACCATCTCATGCAGGGCC AGCAAAAGTGTCACTACATCTGGGTATAGTTTTATGCACTGGTACCAACAG AAACCAGGACAGCCACCCAAACTCCTCATCTATCTTGCATCCAACCTAGAA CCTGGGGTCCCTGCCAGGTTCAGTGGCAGTGGGTCTGGGACAGACTTCGCC CTCAACATCCTTCCTGTGGAGGAGGAGGATGCTGCAACCTATTACTGTCAG CACAGTCGGGAGCTTCCGTACACGTTCGGAGGGGGGACCAAACTGGAAATG AAACGGGCTGATGCTGCACCAACTGTATCCATCTTCCCACCATCCAGTGAG CAGTTAACATCTGGAGGTGCCTCAGTCGTGTGCTTCTTGAACAACTTCTAC CCCAAAGACATCAATGTCAAGTGCAAGATTGATGGCAGTGAACGACAAAAT GGCGTCCTGAACAGTTGGACTGATCAGGACAGCAAAGACAGCACCTACAGC ATGAGCAGCACCCTCACGTTGACCAAGGACGAGTATGAACGACATAACAGC TATACCTGTGAGGCCACTCACAAGACATCAACTTCACCCATTGTCAAGAGC TTCAACAGGAATGAGTGTTAGAGACAAAGGTCCTGAGACGCCACCACCAGC TCcCCAGCTCCATCCTATCTTCCCTTCTAAGGTCTTGGAGGCTTCCCCACA AGCGACCTACCACTGTTGCGGTGCTCCAAACCTCCTCCCCACCTCCTTCTC CTCCTCCTCCCTTTCCTTGGCTTTTATCATGCTAATATTTGCAGAAAATAT TCAATAAAAGTGAGTCTTTGCACTTGAAAAAAAAAAAAAAAAAAAAAAA CTCGAG |

Hereinafter, the formulating methods and kinds of excipients will be described, but the present invention is not limited to them. The representative preparation examples were described as follows.

Preparation of Injection

| | |
|---|---|
| Anti-IRC85 monoclonal antibody (SEQ ID No. 5 and 6) | 20 mg |
| Sodium metabisulfite | 3.0 mg |
| Methyl paraben | 0.8 mg |
| Propyl paraben | 0.1 mg |
| Distilled water for injection | optimum amount |

Injection preparation was prepared by dissolving active component, controlling pH to about 7.5 and then filling all the components in 2 ml ample and sterilizing by conventional injection preparation method.

Preparation of Powder

| | |
|---|---|
| Anti-IRC85 monoclonal antibody (SEQ ID No. 5 and 6) | 10 mg |
| Corn Starch | 100 mg |
| Lactose | 100 mg |
| Talc | 10 mg |

Powder preparation was prepared by mixing above components and filling sealed package.

Preparation of Tablet

| | |
|---|---|
| Anti-IRC85 monoclonal antibody (SEQ ID No. 5 and 6) | 10 mg |
| Corn Starch | 100 mg |
| Lactose | 100 mg |
| Magnesium stearate | optimum amount |

Tablet preparation was prepared by mixing above components and entabletting.

Preparation of Capsule

| | |
|---|---|
| Anti-IRC85 monoclonal antibody (SEQ ID No. 5 and 6) | 10 mg |
| Lactose | 50 mg |
| Corn starch | 50 mg |
| Talc | 2 mg |
| Magnesium stearate | optimum amount |

Tablet preparation was prepared by mixing above components and filling gelatin capsule by conventional gelatin preparation method.

Preparation of Liquid

| | |
|---|---|
| Anti-IRC85 monoclonal antibody (SEQ ID No. 5 and 6) | 20 mg |
| Sugar | 20 g |
| Polysaccharide | 20 g |
| Lemon flavor | 20 g |

Liquid preparation was prepared by dissolving active component, and then filling all the components in 1000 ml ample and sterilizing by conventional liquid preparation method.

Preparation of Health Food

| | |
|---|---|
| Anti-IRC85 monoclonal antibody (SEQ ID No. 5 and 6) | 1000 mg |
| Vitamin mixture | optimum amount |
| Vitamin A acetate | 70 mg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 mg |
| Vitamin C | 10 mg |
| Biotin | 10 mg |
| Amide nicotinic acid | 1.7 mg |
| Folic acid | 50 mg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above mentioned vitamin and mineral mixture may be varied in many ways. Such variations are not to be regarded as a departure from the spirit and scope of the present invention.

Preparation of Health Beverage

| | |
|---|---|
| Anti-IRC85 monoclonal antibody (SEQ ID No. 5 and 6) | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the novel anti-IRC85 monoclonal antibody specifically binding with IRC85 showed potent effect in removing the infected/phagocytosed bacteria from THP-1, a monocytic cell that expresses human IRC85 and is infected with *Listeria monocytogenes* or MDR-*tubercle bacillus*. Accordingly, it can be useful as a medicament and health care food in the prevention and treatment of tuberculosis disease and enteritis disease.

SEQUENCE LIST TEXT

SEQ ID. No. 1: 5'-CGGGATCCGAATTCGGTAC-CCGTCCCATCCTGGAAGTGCCAGAG-3' is sense primer of ICR85, SEQ ID. No. 2: 5'-CGGGATCCGAATTCGG-TACGATGAAGTTGCCATTCTGCCTGCC-3' is antisense primer of ICR85, SEQ ID. No. 3: 5'-CGCGGATCCCAG-CAGGCAAAGTACCAG-3' is sense primer of ICR85-His, SEQ ID. No. 4: 5'-GACAAGCTTCAGGCTCTTTCCTG-GCC-3' is antisense primer of ICR85-H is, SEQ ID. No. 5: MGRLTSSFLLLIVPAYVLSQVTLKESG-PGILQPSQTLSLTCSFSGISLTTSG-MGVGWIRQPSGEGLEWLADIFWDDN KYYNPSLK-SRLTISKDTSTKQVFFKITSVDTADTATYYCVRVYYK NDGYFDVWGAGTTVTVSSAKTTPPSVYPLAPG SAAQTNSMVTLGCLVKGYFPEP-VTVTWNSGSLSSGVHTFPAVLQSD-LYTLSSSVTVPSSTWPSETVTCNVAHPASST KVDK-KIVPRDCGCKPCICTVPEVSSVFIFPPKPKDVLTITLTP KVTCVVVDISKDDPEVQFSWFVDDVEVHTAQTQP REEQFNSTFRSVSELPIMHQDWL-NGKEFKCRVNSAAFPAPIEKTISKTKGR-PKAPQVYTIPPPKEQMAKDKVSLTCM ITDFF-PEDITVEWQWNGQPAENYKNTQPIMDTDGSYFVYS KLNVQKSNWEAGNTFTCSVLHEGLH-NHHTEKSLSHSP GK is heavy chain amino acid sequence of novel anti-ICR85 antibody, SEQ ID. 6: METDTLLLWV-LLLWVPGSTGDIVLTQSPASLAVSLGQ-RATISCRASKSVTTSGYSFMHWYQQK-PGQPPKLLIYLASN LEPGVPARFSGSGSGTD-FALNILPVEEEDAATYYCQHSRELPYT-FGGGTKLEMKRADAAPTVSIFPPSSEQLTSGGA SVVCFLNNFYPKDINVKWKIDGSER-QNGVLNSWTDQDSKDSTYSMSSTLTLT-KDEYERHNSYTCEATHKTSTSPIVK SFNRNEC is light chain amino sequence of novel anti-ICR85 antibody, SEQ ID. 7: TTCAAATGCAGGGTCAACAGTG-CAGCTTTCCCTGCCCCCATCGAGAAAAC-CATCTCCAAAACCAAAGGCAGACCGAA GGCTCCA-CAGGTGTACACCATTCCACCTCCCAAGGAGCAGAT GGCCAAGGATAAAGTCAGTCTGACCTGCATGATAA CAGACTTCTTCCCTGAAGACATTACT-GTGGAGTGGCAGTGGAATGGGCAGC-CAGCGGACACAGATGGCTCTTACTTCGTCTACAGCAA GCTCAATGTGCAGAAGAGCAACTGGGAG-GCAGGAAA TACTTTCACCTGCTCTGTGTTACAT-GAGGGCCTGCACAACCACCATACT- GAGAAGAGCCTCTCCCACTCTCCTGGTA AATGATCCCAGTGTCCTTGGAGC- CCTCTGGTCCTACAGGACTCTGACAC- CTACCTCCACCCCTCCCTGTATAAATAA AGCAC- CCAGCACTGCCTTGNGACCCTGCNAANAAAAAAA AAAAAAAAAAAAAAAAACTCGAG is heavy chain amino acid of novel anti-ICR85 antibody, SEQ ID. 8: GAATTCG- GCACGAGGGAGATGGAGACAGACA- CACTCCTGTTATGGGTACTGCT- GCTCTGGGTTCCAGGTTCCACTGG TGACATTGTGCTGACACAGTCTCCTGCT- TCCTTAGCTGTTTCTCTGGGGCA- GAGGGCCACCATCTCATGCAGGGCCA GCAAAAGT- GTCACTACATCTGGGTATAGTTTTATGCACTGGTACC AACAGAAACCAGGACAGCCACCCAAACTCCTC ATCTATCTTGCATCCAACCTAGAAC- CTGGGGTCCCTGCCAGGTTCAGTG- GCAGTGGGTCTGGGACAGACTTCGCCCT CAA- CATCCTTCCTGTGGAGGAGGAGGATGCTGCAACCT ATTACTGTCAGCACAGTCGGGAGCTTC- CGTACACGTTCG GAGGGGGGACCAAACTGGAAAT- GAAACGGGCTGATGCTGCACCAACTG- TATCCATCTTCCCACCATCCAGTGAGCAG TTAACATCTGGAGGTGCCTCAGTCGTGT- GCTTCTTGAACAACTTCTACCCCAAAGA- CATCAATGTCAAGTGGAAGAT TGATGGCAGTGAAC- GACAAAATGGCGTCCTGAACAGTTGGACTGATCAG GACAGCAAAGACAGCACCTACAGCATGA GCAG- CACCCTCACGTTGACCAAGGACGAGTAT- GAACGACATAACAGCTATACCTGTGAG- GCCACTCACAAGACATCA ACTTCACCCATTGTCAAGAGCTTCAA- CAGGAATGAGTGTTAGAGACAAAGGTC- CTGAGACGCCACCACCAGCTCcCC AGCTCCATC- CTATCTTCCCTTCTAAGGTCTTGGAGGCTTCCCCAC AAGCGACCTACCACTGTTGCGGTGCTCCAAAC CTC- CTCCCCACCTCCTTCTCCTCCTCCTC- CCTTTCCTTGGCTTTTATCAT- GCTAATATTTGCAGAAAATATTCAATA AAAGTGAGTCTTTGCACT- TGAAAAAAAAAAAAAAAAAAAAAAAAACTCGAG is light chain amino acid sequence of novel anti-ICR85 antibody, SEQ ID. 9: 5'-gagagagagagagagagagaactagtctcgagtt-3' is XhoI cognition nucleotide sequence, SEQ ID. 10: 5'-gaactctggatccctgtcca-3' is CH1 domain binding G-1U primer of mouse IgG1 cDNA, SEQ ID. 11: 5'-tgcaaggctta-caaccacaa-3' is CH1 domain binding G-1D primer of mouse IgG1 cDNA, SEQ ID. 12: 5'-atcttcccaccatccagtga-3' is CH1 domain binding K-IU primer of mouse kappa chain cDNA, SEQ ID. 13: 5'-cgtccttggtcaacgtgag-3' is CH1 domain binding K-1D primer of mouse kappa chain cDNA.

The invention claimed is:

1. An isolated anti-IRC85 monoclonal antibody comprising:
   an amino acid sequence that comprises
   a heavy chain region (H) of SEQ ID NO: 5; and
   a light chain region (L) of SEQ ID NO: 6.

2. An isolated anti-IRC85 monoclonal antibody comprising:
   a heavy chain amino acid sequence encoded by a nucleotide sequence comprising SEQ ID NO: 7; and
   a light chain amino acid sequence encoded by a nucleotide sequence comprising SEQ ID NO: 8.

3. The antibody of claim 1 or 2, wherein said antibody comprises a heavy chain variable region (VH) that comprises amino acid sequences of SEQ ID NO: 14 (HCDR1),
   SEQ ID NO: 15 (HCDR2), and
   SEQ ID NO: 16 (HCDR3).

4. The antibody of claim 1 or 2, wherein said antibody comprises a light chain variable region (VL) that comprises amino acid sequences of
   SEQ ID NO: 19 (LCDR1),
   SEQ ID NO: 20 (LCDR2), and
   SEQ ID NO: 21 (LCDR3).

5. An isolated anti-IRC85 antibody comprising:
   a heavy chain variable region (VH) that comprises amino acid sequences of
   SEQ ID NO: 14 (HCDR1),
   SEQ ID NO: 15 (HCDR2), and
   SEQ ID NO: 16 (HCDR3); and
   a light chain variable region (VL) that comprises amino acid sequences of
   SEQ ID NO: 19 (LCDR1),
   SEQ ID NO: 20 (LCDR2), and
   SEQ ID NO: 21 (LCDR3).

* * * * *